United States Patent [19]
Bachman et al.

[11] Patent Number: 6,152,896
[45] Date of Patent: *Nov. 28, 2000

[54] MANUAL BREAST PUMP

[75] Inventors: Rebecca J. Bachman, Fremont; Karen L. Celata, Grand Haven, both of Mich.; Mark A. Gilbertson, Sauk City, Wis.; Edward A. Raleigh, Waunakee, Wis.; Jeffery R. Staszak, Madison, Wis.; John W. Grosz, Columbus, Wis.

[73] Assignee: Gerber/Baby Care, Fremont, Mich.

[ * ] Notice: This patent is subject to a terminal disclaimer.

[21] Appl. No.: 09/159,618

[22] Filed: Sep. 23, 1998

Related U.S. Application Data

[63] Continuation of application No. 08/629,278, Apr. 8, 1996, Pat. No. 5,843,029.
[60] Provisional application No. 60/005,321, Oct. 16, 1995.

[51] Int. Cl.[7] ........................................ A61M 1/26
[52] U.S. Cl. .............................. 604/74; 604/346
[58] Field of Search ........................ 604/74, 73, 75, 604/76, 115, 315, 346, 316

[56] References Cited

U.S. PATENT DOCUMENTS

| | | |
|---|---|---|
| D. 251,015 | 2/1979 | Cone . |
| D. 283,732 | 5/1986 | Elliott . |
| D. 295,896 | 5/1988 | Van Meter et al. . |
| D. 299,537 | 1/1989 | Morifuji . |
| D. 307,478 | 4/1990 | Morifuji . |
| D. 309,500 | 7/1990 | Yuan et al. . |
| D. 313,103 | 12/1990 | Kawano . |
| D. 326,319 | 5/1992 | Chambers . |
| D. 326,516 | 5/1992 | Chambers . |
| D. 345,209 | 3/1994 | Shoda et al. . |
| 790,051 | 5/1905 | Halstead . |
| 793,940 | 7/1905 | Kramer et al. . |
| 897,289 | 9/1908 | Howell . |
| 1,484,874 | 2/1924 | Del Castillo . |
| 1,509,226 | 9/1924 | Brown . |
| 1,596,520 | 8/1926 | Eskholme et al. . |
| 1,880,354 | 10/1932 | Mueller . |
| 2,209,424 | 7/1940 | Shipman et al. . |
| 2,303,393 | 12/1942 | Schmidt . |
| 2,558,479 | 6/1951 | Miller . |
| 3,424,486 | 1/1969 | Corley . |
| 3,637,129 | 1/1972 | Kaufman . |
| 3,695,266 | 10/1972 | Lussier . |
| 3,738,363 | 6/1973 | Lunas et al. . |
| 3,782,385 | 1/1974 | Loyd . |
| 3,822,703 | 7/1974 | Davisson . |
| 3,911,920 | 10/1975 | Susinn . |

(List continued on next page.)

FOREIGN PATENT DOCUMENTS

| | | |
|---|---|---|
| 466462A1 | 1/1992 | European Pat. Off. . |
| 1051198 | 2/1959 | Germany . |
| 3605083 | 8/1987 | Germany . |
| 8714995 | 2/1988 | Germany . |
| 762701 | 12/1956 | United Kingdom . |
| 2082920 | 3/1982 | United Kingdom . |
| 2166353 | 5/1986 | United Kingdom . |

*Primary Examiner*—John D. Yasko
*Attorney, Agent, or Firm*—Price, Heneveld, Cooper, DeWitt & Litton

[57] ABSTRACT

A manual breast pump adapted for one-handed operation includes a pump body defining an inlet, an outlet and a vacuum port, a stationary handle connected to the pump body, and a movable handle connected to the manual breast pump and spaced from the stationary handle so that both handles can be grasped simultaneously between the palm and fingers of a hand. The movable handle is movable with respect to the stationary handle and is operably connected to a piston disposed within the pumping chamber so that movement of the movable handle with respect to the stationary handle results in movement of the piston within the pumping chamber to create a vacuum at the vacuum port. The invention provides a manual breast pump which can be easily and comfortably supported and operated using one hand.

33 Claims, 10 Drawing Sheets

U.S. PATENT DOCUMENTS

| | | |
|---|---|---|
| 3,921,249 | 11/1975 | Fortune . |
| 3,977,405 | 8/1976 | Yanase . |
| 4,020,838 | 5/1977 | Phillips et al. . |
| 4,033,346 | 7/1977 | Phillips et al. . |
| 4,263,911 | 4/1981 | McCormack et al. . |
| 4,263,912 | 4/1981 | Adams . |
| 4,573,969 | 3/1986 | Schlensog et al. . |
| 4,583,970 | 4/1986 | Kirchner . |
| 4,673,388 | 6/1987 | Schlensog et al. . |
| 4,680,028 | 7/1987 | Stuart . |
| 4,759,747 | 7/1988 | Aida et al. . |
| 4,799,922 | 1/1989 | Beer et al. . |
| 4,813,932 | 3/1989 | Hobbs . |
| 4,857,051 | 8/1989 | Larsson . |
| 4,892,517 | 1/1990 | Yuan et al. . |
| 4,929,229 | 5/1990 | Larsson . |
| 4,954,054 | 9/1990 | Neward . |
| 4,961,726 | 10/1990 | Richter . |
| 4,964,851 | 10/1990 | Larsson . |
| 4,968,303 | 11/1990 | Clarke et al. . |
| 4,998,915 | 3/1991 | Hannah . |
| 5,007,899 | 4/1991 | Larsson . |
| 5,009,638 | 4/1991 | Riedweg et al. . |
| 5,049,126 | 9/1991 | Larsson . |
| 5,071,403 | 12/1991 | Larsson . |
| 5,188,610 | 2/1993 | Rains . |
| 5,241,969 | 9/1993 | Carson et al. . |
| 5,277,557 | 1/1994 | Cooper . |
| 5,295,957 | 3/1994 | Aida et al. . |
| 5,304,129 | 4/1994 | Forgach . |
| 5,358,476 | 10/1994 | Wilson . |
| 5,408,919 | 4/1995 | Hutzler et al. . |
| 5,415,632 | 5/1995 | Samson . |
| 5,662,268 | 9/1997 | Katzenberger . |
| 5,843,029 | 12/1998 | Bachman et al. .......... 604/74 |

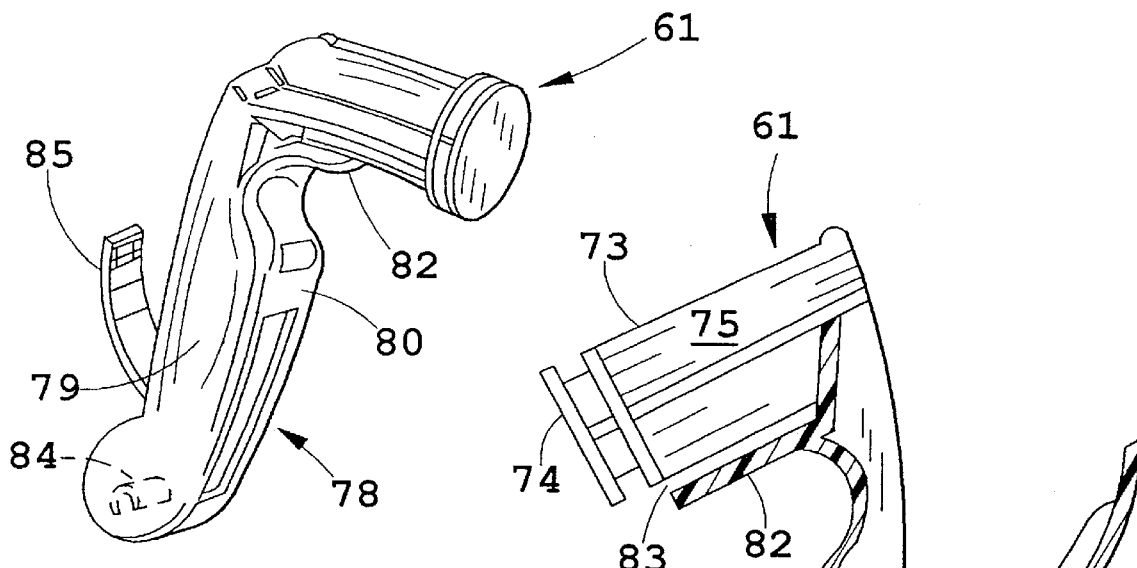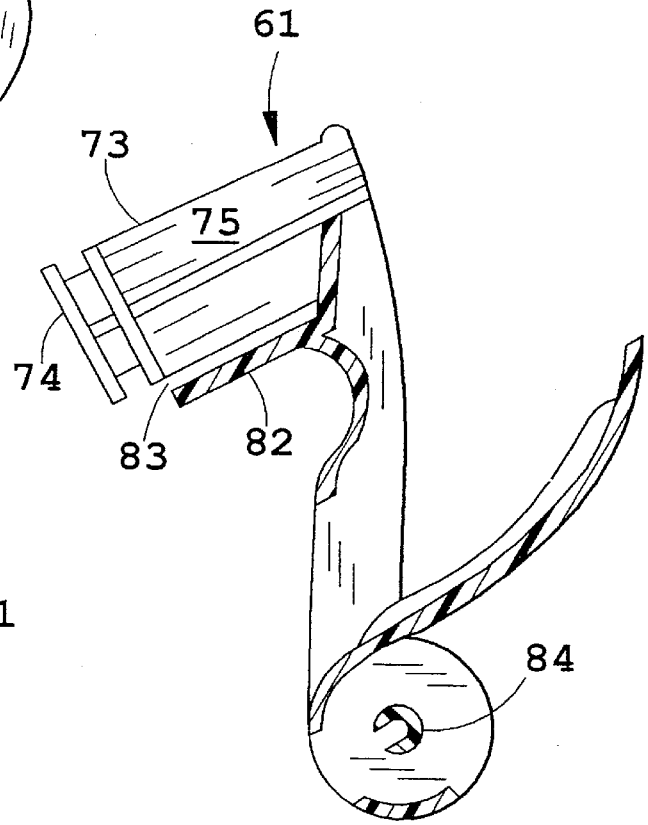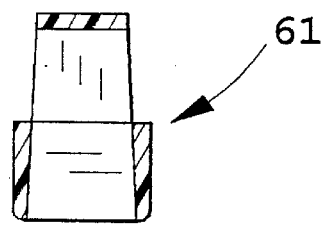
FIG.12
FIG.13
FIG.14
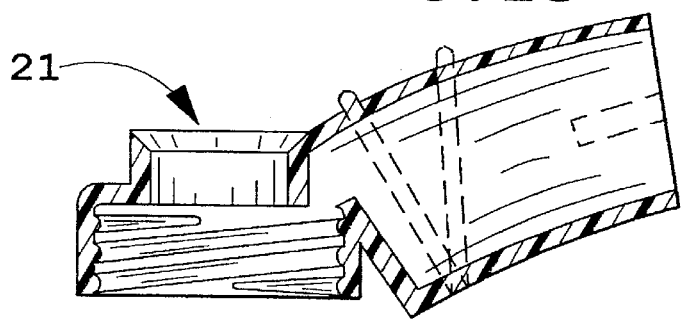
FIG.16
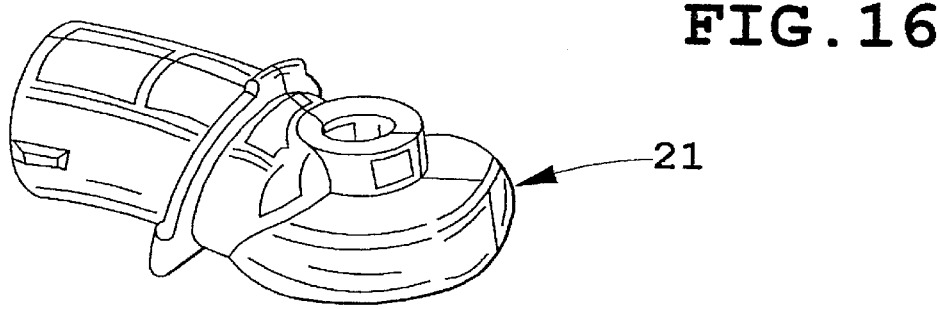
FIG.15

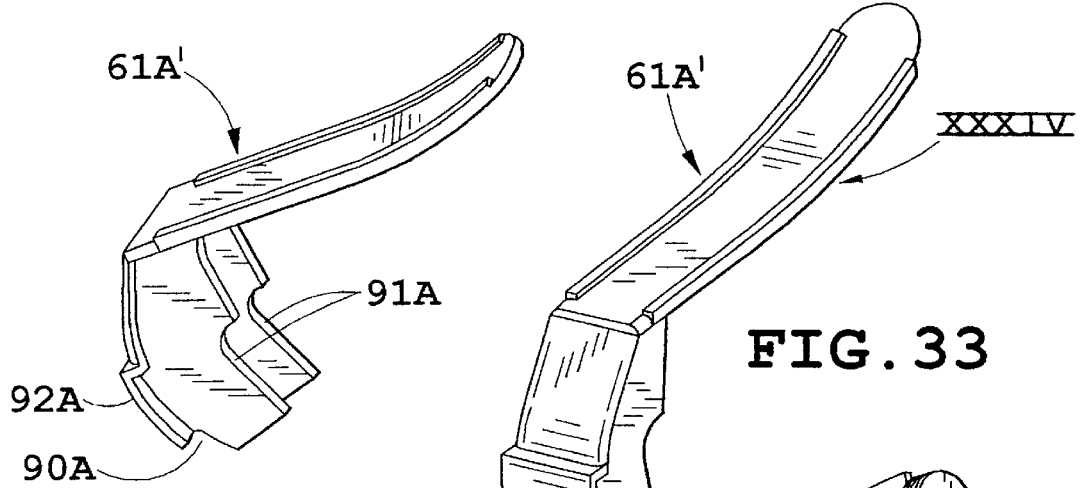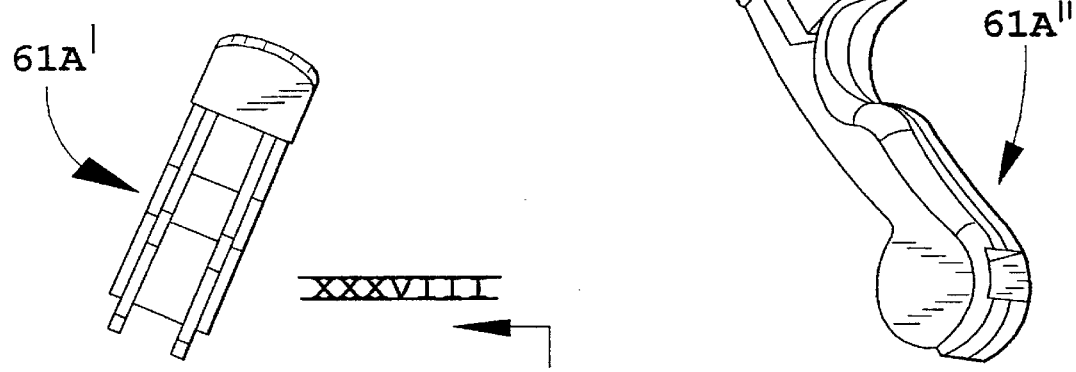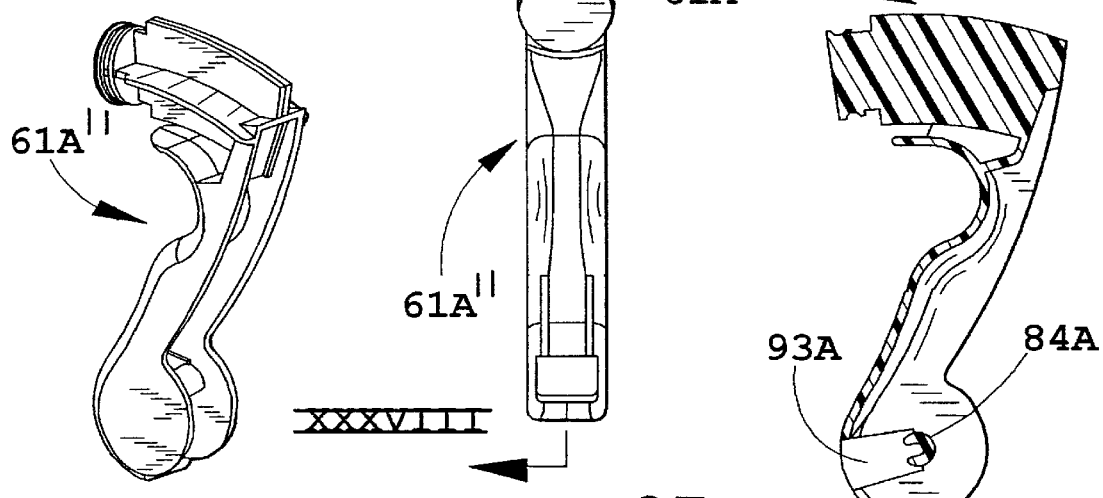

MANUAL BREAST PUMP

This application claims the benefit of U.S. Provisional Application No. 60/005,321, filed Oct. 16, 1995 and is a continuation of Ser. No. 08/629,278 filed Apr. 8, 1996 now U.S. Pat. No. 5,843,029.

BACKGROUND OF THE INVENTION

This invention relates to a manually operated breast pump, and more particularly to a manually operated breast pump which can be supported and operated using one hand, and which can be easily disassembled for cleaning and sanitizing.

It is generally desirable to manually stimulate the breast to encourage lactation during withdrawal of milk using a breast pump. For this reason, it is preferable that the manual breast pump be capable of being operated using only one hand so that the other hand can be used to encourage lactation. However, most know manual breast pumps require two-handed operation, one hand holding the milk-receiving vessel and the other hand operating the manual suction device. For example, many manual breast pumps include a cylinder defining a suction chamber and a piston which is reciprocated with respect to the suction chamber to create a vacuum. Other similar manual breast pumps include a cylinder defining a suction chamber and having a second cylinder slidably received over the cylinder defining the suction chamber. Operation of many of these types of breast pumps require the use of one hand to support the milk-receiving vessel or part of the manual breast pump, while the other hand is used to reciprocate the piston or outer cylinder. Many other breast pumps, especially older designs, employ a squeeze bulb which is connected by a flexible conduit to a pump body. In order to use these types of breast pumps, the pump body must be supported in one hand while the bulb is squeezed with the other hand.

Some manual breast pumps have been designed for one-handed operation, but they have generally been awkward to use. For example, many manual breast pumps designed for one-handed operation require that the operator support the pump and bottle with their thumb, such as by inserting the thumb through a thumb ring or wrapping the thumb around the neck connecting the breast shield or funnel to the pump body, while using their fingers to push a lever or handle toward the thumb supporting the pump and milk-receiving vessel. Operation of these types of manual breast pumps can be awkward, difficult, fatiguing, and uncomfortable. In particular, the pump and milk-receiving vessel are largely supported by the thumb, and the required operating movement tends to exert a moment on the pump and milk-receiving vessel about the thumb which must generally be opposed by the breast.

Still another disadvantage with manual breast pumps designed for one-handed use is that they have been relatively complicated and difficult to disassemble for cleaning and sanitation. For example, manual breast pumps designed for one-handed operation have generally included co-operating piston and cylindrical suction chamber arrangements which are integrally connected to the portion of the pump which is secured to the milk-receiving vessel, and wherein the piston is not removable from the cylindrical suction chamber. As a result, it is generally difficult to thoroughly clean and disinfect the pump, especially the internal portions of the suction chamber.

Another disadvantage with known manual breast pumps is that a piston or other reciprocating member must be moved linearly through a straight cylinder during operation. In order to effect such linear movement during operation of the manual breast pump, it is generally necessary to provide a relatively complicated pump mechanism comprising a large number of components which are difficult to assemble and disassemble, and/or require the operator to make awkward and uncomfortable pumping movements.

A further problem with known manual breast pumps is that they generally either do not include a one-way valve between the manual breast pump and the milk-receiving vessel, or, if they do, it is a relatively complicated, multiple component valve arrangement such as ball or plug-type valve arrangement. A one-way valve which allows milk to flow into the milk-receiving vessel, but which prevents milk from flowing back from the milk-receiving vessel into the pump body is highly desirable. However, it is also desirable to achieve the one-way valve function with a simpler, less expensive device, which will reduce the overall cost of the manual breast pump and allow easier assembly and disassembly for cleaning and sanitizing of the components of the manual breast pump.

SUMMARY OF THE INVENTION

This invention provides a manual breast pump which can be easily and comfortably supported and operated using one hand. The manual breast pump is comprised of relatively few components which can be quickly and easily assembled and disassembled to facilitate thorough cleaning and disinfecting thereof.

The manual breast pump includes a pump body which defines an inlet which is in fluid communication with a breast engaging funnel, an outlet for sealingly engaging an opening in a milk-receiving vessel, and a vacuum port in fluid communication with a tubular pump chamber. A stationary handle is connected to the pump body, and a movable handle is connected to the manual breast pump. The movable handle is spaced from the stationary handle so that both handles can be grasped simultaneously between the palm and fingers of a hand. The movable handle is movable with respect to the stationary handle and is operably connected to a piston disposed within the pump chamber so that movement of the movable handle with respect to the stationary handle results in movement of the piston within the pump chamber to create a vacuum at the vacuum port.

In accordance with a preferred aspect of the invention, a manual breast pump is provided which is comprised of a relatively small number of parts that can be quickly and easily assembled or disassembled. Desirably, many of the components are configured to be snapped together and snapped apart to facilitate assembly and disassembly for easy cleaning and sanitizing of the components.

The manual breast pump preferably includes, in accordance with a further aspect of the invention, an arcuate pump chamber which cooperates with a piston operably connected to a pump actuating lever. The piston is reciprocated along an arcuate path within the arcuate pump chamber by operation of a movable handle or other pump actuating lever. The arcuate pump chamber and arcuate movement of the piston allows the movable handle to be moved with respect to a stationary handle using a more natural and comfortable pumping motion wherein the handle portions are squeezed between the palm and fingers of a hand. The arcuate piston and pump chamber arrangement also provides a very simple mechanical arrangement requiring few components, further facilitating assembly and disassembly.

In another aspect of the invention, a one part back splash valve is disposed at an outlet of a pump body engaging an opening in a milk-receiving vessel. The back splash valve is a one-way valve which allows milk to enter the milk-receiving vessel from the pump body, but which prevents milk from the milk-receiving vessel from flowing back into the pump body. The one piece back splash valve includes an annular seal lip for sealing between the outlet of the pump body and the upper edges or lip of the milk-receiving vessel. The valve comprises a pair of opposing flexible lips which flex apart to allow milk to flow through the valve from the pump body into the milk-receiving vessel, but which collapse together to prevent milk from flowing in the opposite direction.

In accordance with a further aspect of the invention, a conduit neck has a first end configured to sealingly and rotatably engage the inlet of the pump body. A second end of the conduit neck is configured to support a breast engaging funnel. The rotatable conduit neck provides fluid communication between the breast engaging funnel and the inlet to the pump body, while allowing rotation of the breast engaging funnel with respect to pump handle portions attached to the pump body, as desired, to achieve maximum comfort during operation of the manual breast pump.

BRIEF DESCRIPTION OF THE DRAWINGS

FIG. 12 is a perspective view of the movable handle shown in FIG. 1;

FIG. 13 is a cross-sectional view of the movable handle shown in FIG. 12;

FIG. 14 is a cross-sectional view of the movable handle shown in FIG. 13;

FIG. 15 is a perspective of the pump body shown in FIG. 1;

FIG. 16 is a cross-sectional view of the pump body shown in FIG. 15;

FIGS. 32–33 are perspective views of the spring device shown in FIG. 18;

FIG. 34 is an end view taken in the direction 34 in FIG. 33;

FIGS. 35–36 are perspective views of the piston handle of the manual hand-pump mechanism shown in FIG. 18;

FIG. 37 is an end view of the piston handle shown in FIG. 35;

FIG. 38 is a cross-sectional view taken along the line XXXVIII—XXXVIII in FIG. 37;

DETAILED DESCRIPTION OF PREFERRED EMBODIMENTS

Figure 1:
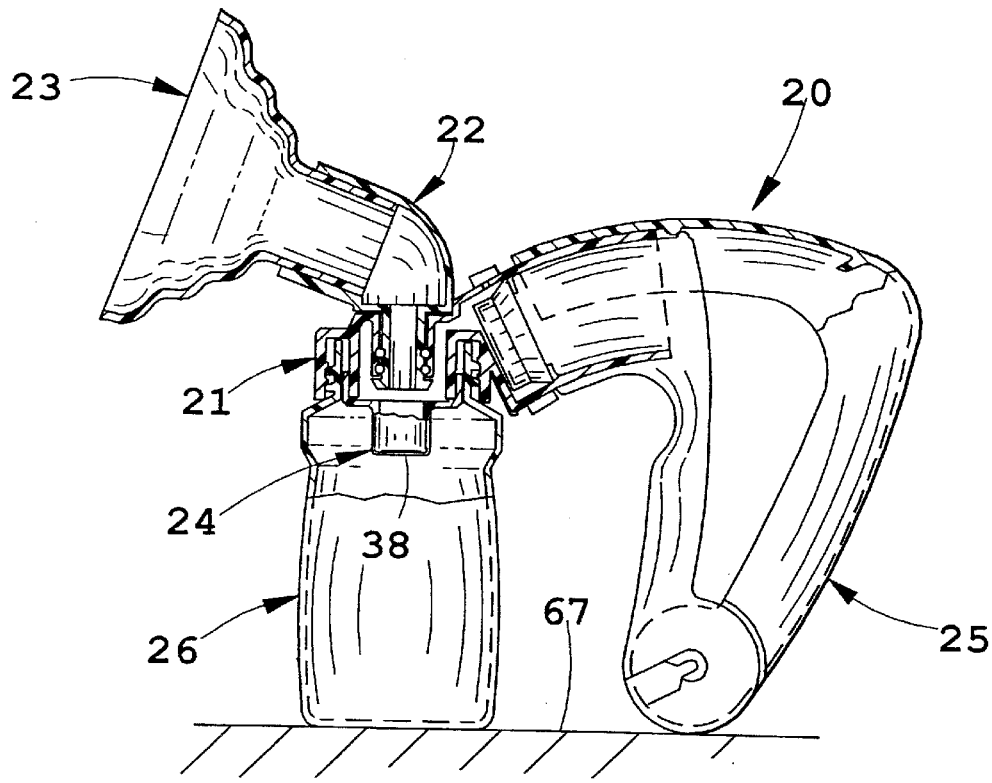
FIG. 1 is a side cross-sectional view of a manual breast pump embodying the present invention.
Figure 2:
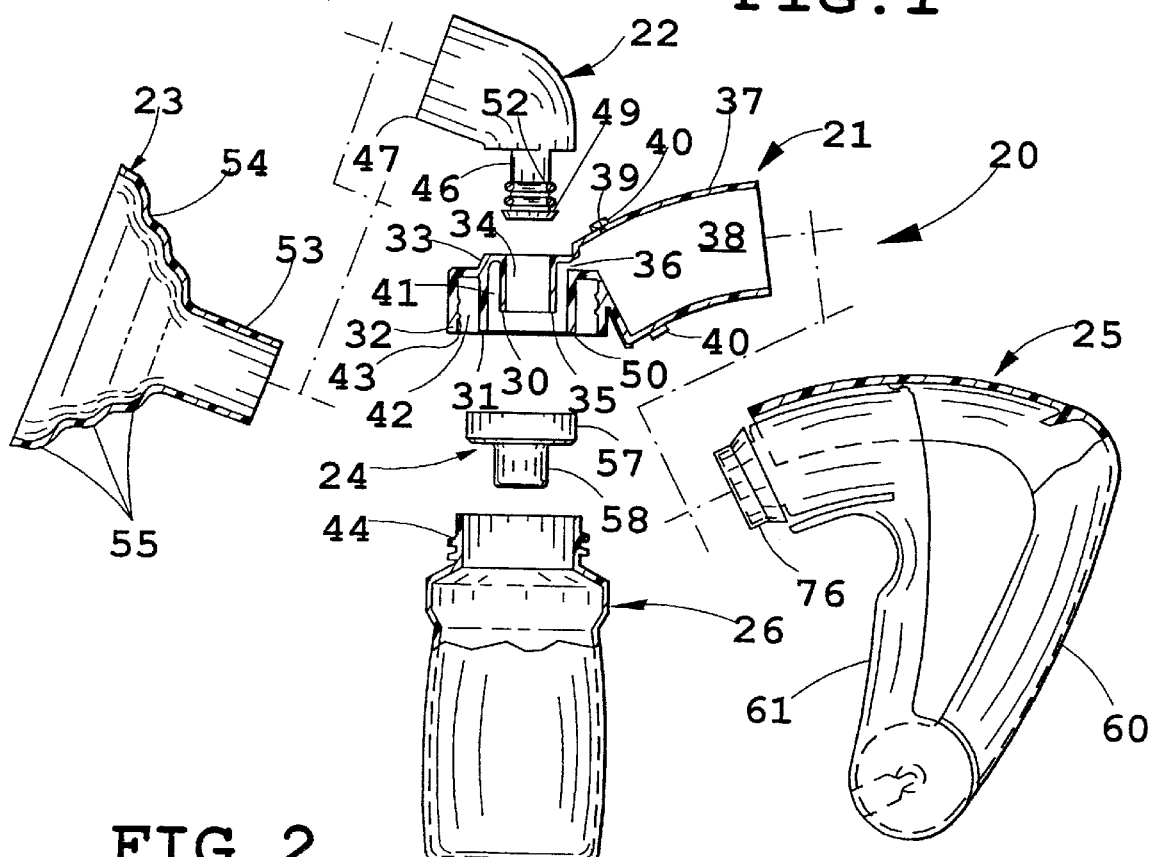
FIG. 2 is an exploded side view of the manual breast pump shown in FIG. 1.

A manual breast pump 20 (FIGS. 1–2) embodying the present invention includes a pump body 21, a funnel-supporting shield neck 22 and funnel 23 connected to an inlet on the pump body 21, a back splash valve 24 connected to an outlet of the pump body 21, and a manually operable hand-pump mechanism 25 connected to a vacuum port on the pump body 21. The breast pump 20 can be connected to a bottle 26 and conveniently and comfortably operated to extract milk from a mother's breast. The breast pump 20 is configured to stably rest on a support surface when the mother has filled the bottle 26 until the mother is ready to take care of the collected milk. The breast pump 20 is also configured to be separated into components that can be sanitarily cleaned such as in an automatic dishwasher.

Pump body 21 (FIG. 2) includes three concentric cylindrically shaped walls 30, 31, and 32 that extend downwardly from a top wall 33. The juncture of inner cylindrical wall 30 and top wall 33 defines a milk inlet 34, and the bottom of inner cylindrical wall 30 defines a milk outlet 35. A vacuum port 36 is defined on one side of top wall 33 generally between cylindrical inner wall 30 and intermediate cylindrical wall 31. A tubular cylindrical sleeve 37 extends arcuately laterally from walls 30–33. A vacuum-release control valve 40 operably covers hole 39, and is operable by thumb or finger pressure to vent pump chamber 38. Cylindrically shaped walls 30–32 extend downwardly and define an inner annular recess 41 and an outer annular recess 42. The inner surface on outer cylindrical wall 32 includes threads 43 for threadably engaging mating threads 44 on the top of bottle 26. The recess 42 is configured to sealingly engage the top of bottle 26.

Neck 22 (FIG. 2) is generally a conduit including a tubular pump-body-engaging lower section 46 and an upper tubular section 47 which is angled with respect to the lower section. The upper tubular section is preferably at about a 20° angle with respect to the lower tubular section. The lower section 46 defines a tubular nipple configured to sealingly frictionally engage inlet 34 on pump body 21. Specifically, lower section 46 includes an outer surface having a detent 49 thereon for frictionally releasably engaging the lower end 50 of inner cylindrical wall 30 and further includes a cylindrical recess for receiving at least one O-ring seal 52. The angled section 47 includes an inner surface for receiving and frictionally engaging a slip-fit cylindrically shaped end 53 of rippled funnel 23. The other end 54 of funnel 24 is frustoconically shaped to generally match the shape of a mother's breast, and includes three concentric annular ripples 55 designed for optimal comfort and sealing engagement with the mother's breast. The material of funnel 23 is resilient and deformable.

Figure 6:
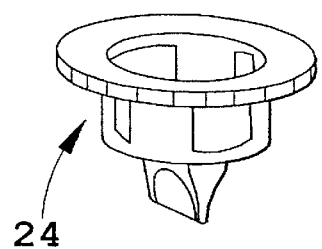
FIG. 6 is a perspective view of the piston seal shown in FIG. 1.
Figure 7:
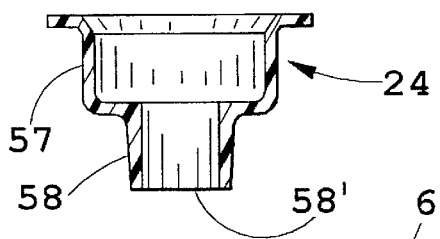
FIG. 7 is a cross-sectional view of the seal shown in FIG. 6.
Figure 8:
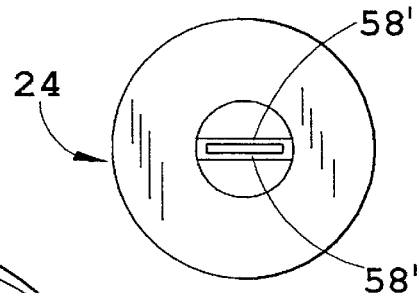
FIG. 8 is a plan view of the seal shown in FIG. 6.

Back splash valve 24 (FIGS. 6–8) includes an annular seal lip 57 and a lip valve element 58 formed at a lower end of valve 24. Valve element 58 comprises a pair of opposing "duck bill" shaped flexible lips 58 that flex apart to permit the flow of milk through the valve into a milk-receiving vessel or bottle 26 in a first direction "A", but which collapse together to prevent the flow of milk in an opposite direction. The shaped body 57 is configured to sealingly engage the pump body 21 and bottle 26. It is contemplated that the shaped body 57 can include different configurations. For example, compare FIG. 1 and FIGS. 6–7. It is also contemplated that the valve 58 can be configured differently. For example, the lip valve shown could be replaced with a gravity-controlled ball-and-seat valve. In the illustrated preferred embodiment (FIG. 1), the intermediate wall 31 extends below inner wall 30 when assembled to allow flow of air through inlet 34 under inner wall 31 and upwardly into vacuum port 36. The valve element 38 extends into bottle 26, such that milk is directed to flow into bottle 26.

Figure 9:
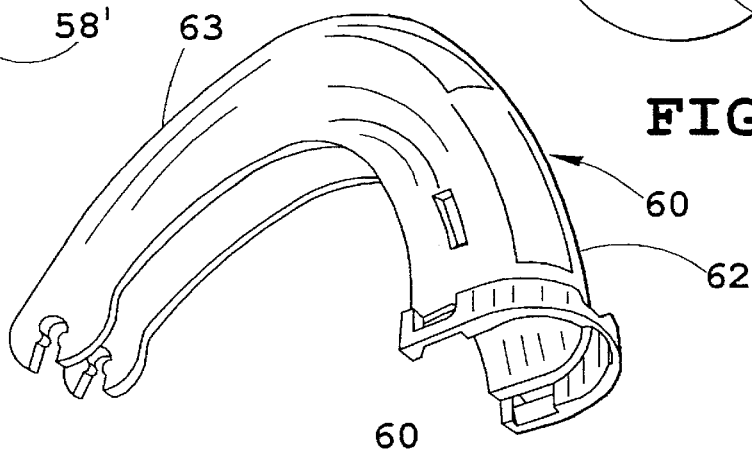
FIG. 9 is a perspective view of the stationary handle shown in FIG. 1.
Figure 11:
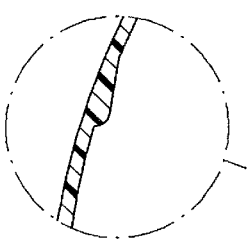
FIG. 11 is an enlarged view of an alternative section for the stationary handle shown in FIG. 10.
Figure 10:
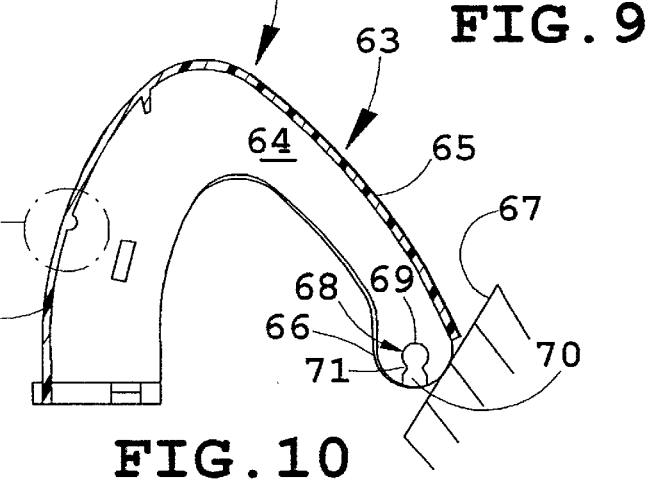
FIG. 10 is a cross-sectional view of the stationary handle shown in FIG. 9.
Figure 17:
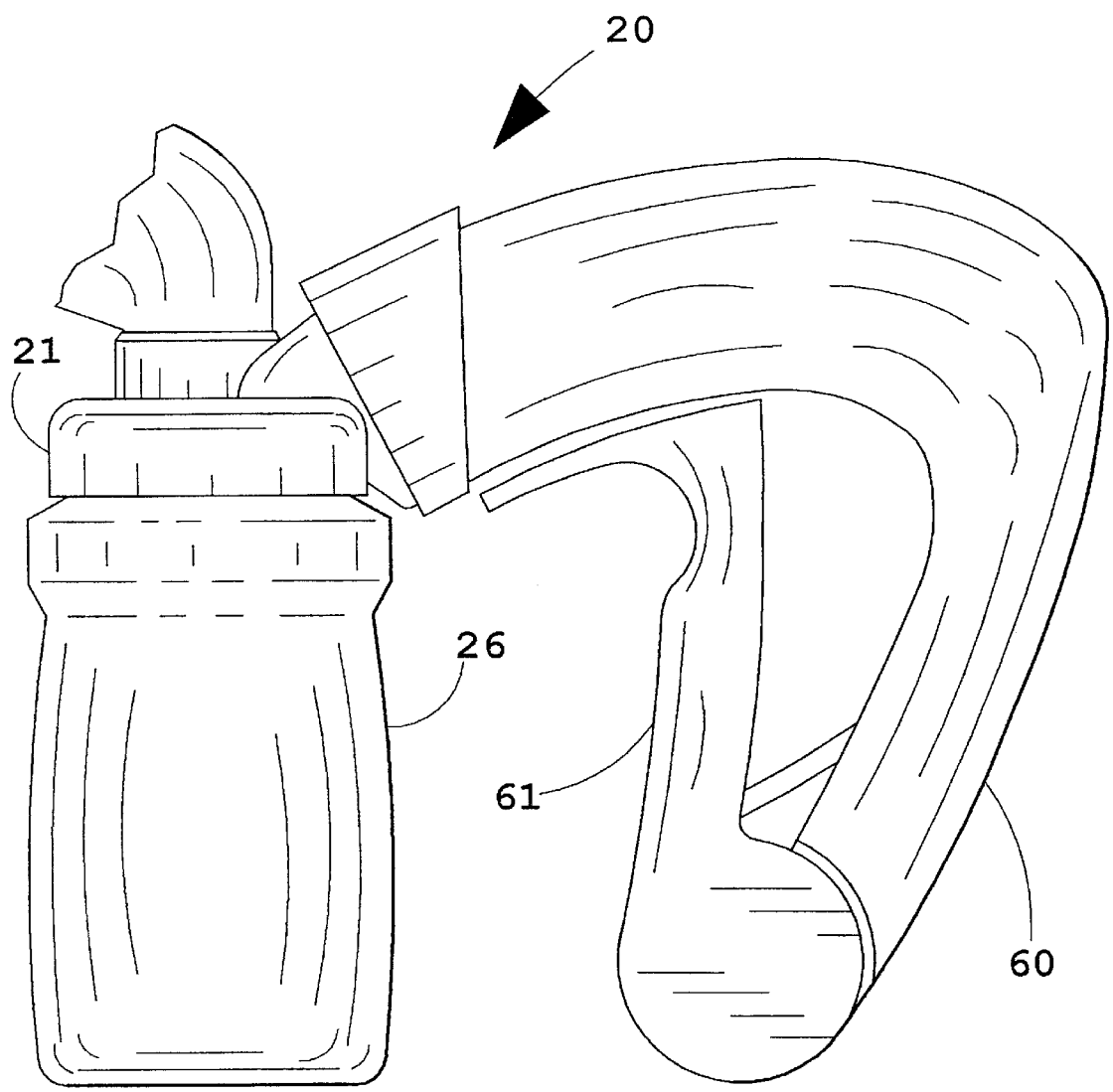
FIG. 17 is a side view of the breast pump shown in FIG. 1.

Hand-pump mechanism 25 includes a stationary handle 60 (FIGS. 9–10) and a movable spring/piston handle 61 (FIGS. 12–13). The stationary handle 60 (FIGS. 9–10) is boomerang shaped, and includes an elongated U-shaped connector section 62 configured for snap-attach connection to the arcuate cylindrically shaped sleeve 37 forming pump chamber 38. Specifically, pump body 21 includes detents 95 which engage apertures 96 in stationary handle 60. A palm-receiving grip 63 extends at an angle to tubular connector section 62. The grip 63 includes side walls 64 connected by a rear wall 65. The side walls 64 and rear wall 65 act as a shroud which protects the pump mechanism 25. The grip 63 also has a lower end 66 configured to stably engage a support surface such as a table top or counter top 67. The lower end 66 and the bottom of the bottle 26 form a structure for stably engaging the flat support surface so that the breast pump 20 including the bottle 26 can be stably rested as a unit on a counter top. A pair of slots 68 are formed in the lower end of side walls 64. The slots 68 include a pivot-forming end 69 and an inlet 70 to the end 69. A detent 71 is formed along the inlet 69.

The spring/piston handle 61 includes a piston-forming section 73 (FIGS. 12–13) having a flat end 74 and an X-shaped cross section elongated piston shaft 75. Piston seal 76 (FIG. 3) includes a lipped pocket 76' configured to releasably engage the flat end 74. Piston seal 76 includes an annular flange 77 for sealingly slidably engaging the inner surface of pump sleeve 37. Spring/piston handle 61 (FIGS. 12–13) further includes an arm section 78 formed by opposing side walls 79 and front wall 80. The front wall 80 includes a wall section 82 that extends adjacent to piston shaft 75 and defines a space 83 for receiving pump sleeve 37 therein. A pivot-forming pin 84 extends between opposing side walls 79. The pin 84 is configured to snap attach into slots 68 and is rotatably held therein by detent 71. A leaf-spring-like finger 85 extends from the bottom of side walls 79 generally tangentially and spirally away from pin 84. It is contemplated that the spring can be a separate, replaceable element. Spring 85 urges piston 73 toward the end of pump chamber 38 adjacent the vacuum port.

Figure 3:
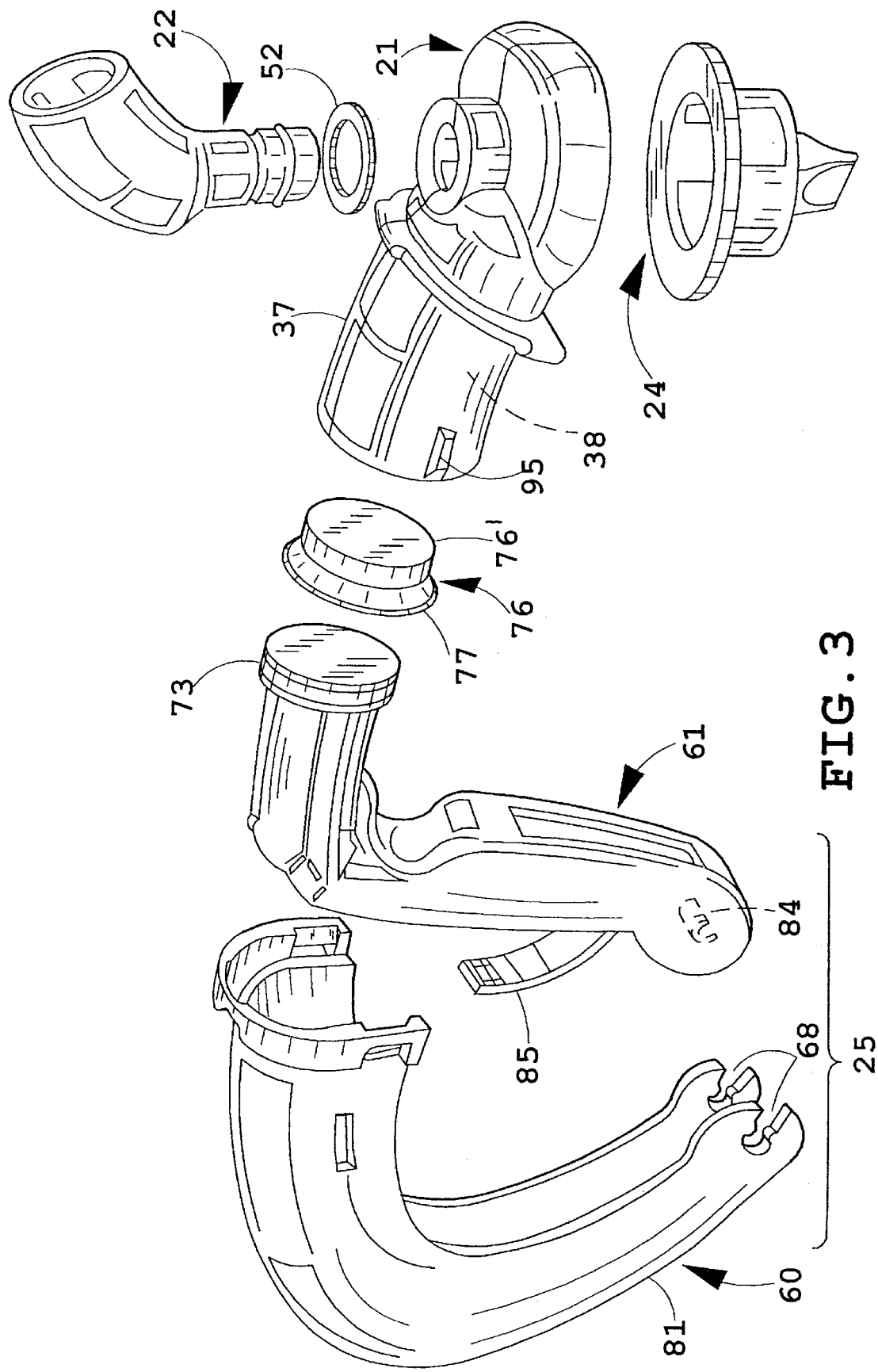
FIG. 3 is an exploded perspective view of the manual breast pump shown in FIG. 1.
Figure 4:
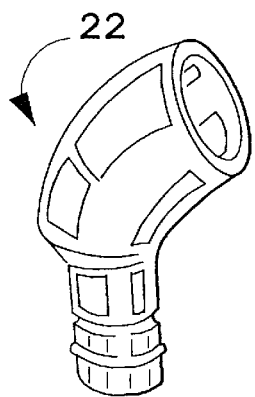
FIG. 4 is a perspective view of the shield neck shown in FIG. 1.
Figure 5:
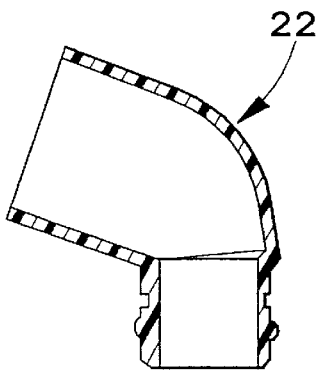
FIG. 5 is a cross-sectional view of the shield neck shown in FIG. 4.

The piston seal 76 is initially installed onto piston-forming section 73. The spring/piston handle 61 is then assembled into stationary handle 60 (FIG. 3). Specifically, pin 84 of spring/piston handle 61 is snap attached into slots 68 of stationary handle 60, thus pivotally mounting spring/piston handle 61 to stationary handle 60. The two are then inserted as a unit onto sleeve 37 of pump body 21. When stationary handle 60 is slip-connected to sleeve 37, piston-forming section 73 forms a piston within chamber 38. Spring finger 85 engages rear wall 81 of handle 60 to bias piston-forming section 73 to a forward position. The front wall 80 forms a finger-actuable trigger that can be comfortably operated while the mother is holding stationary handle 60 with her hand. By "squeezing the trigger", spring/piston handle 61 moves rearwardly against the force of spring finger 85, causing a vacuum to be drawn in chamber 38. The vacuum is communicated through vacuum port 36 and inlet 34 to funnel 24 (FIG. 1), such that milk is drawn into the funnel 23. The milk flows from the funnel through pump body 21 and inlet 34 and, due to the configuration, drops through pump body outlet 35 and back splash valve 22 into bottle 26. When the mother has finished collecting milk, the breast pump 20 and the bottle 26 can be stably set as a unit onto a table top or counter top without fear of tipping over since the configuration includes structure forming a stable support for the pump 20.

Figure 18:
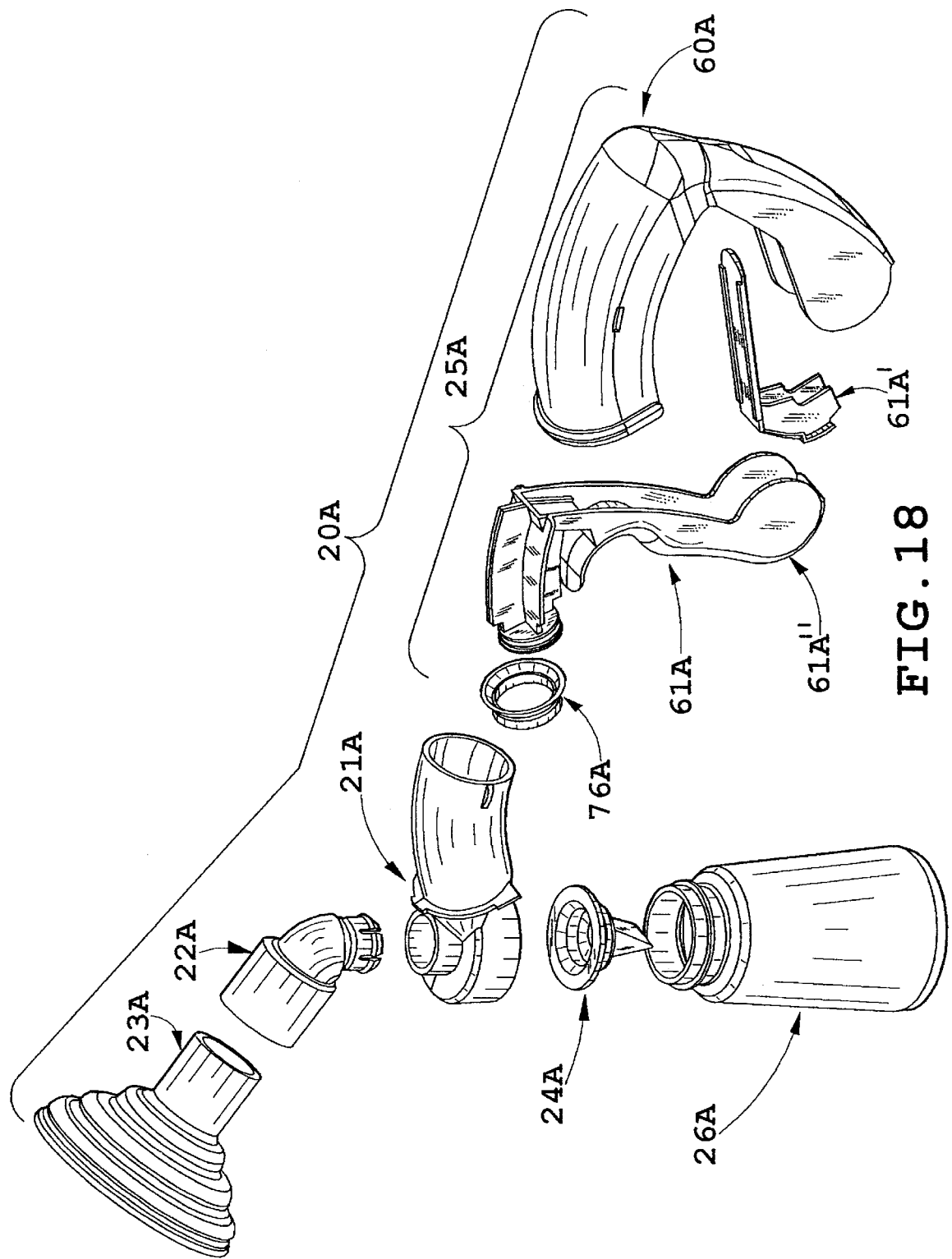
FIG. 18 is an exploded perspective view of a modified manual breast pump embodying the present invention.
Figure 19:
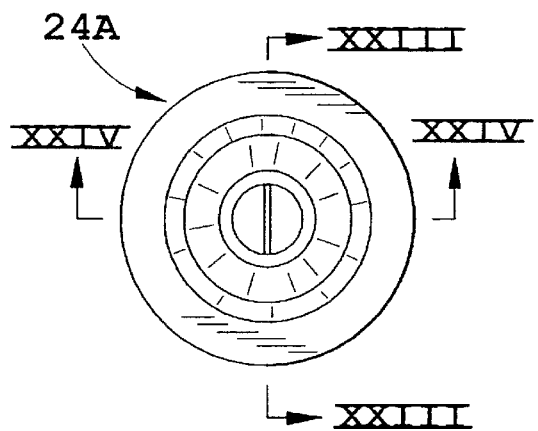
FIGS. 19–22 are top, side, front, and bottom views of the back splash valve shown in FIG. 18.
Figure 20:
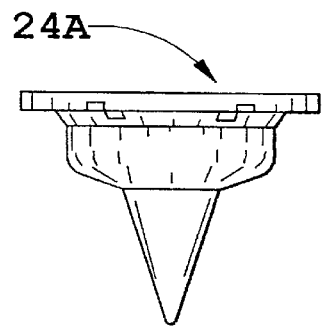
Figure 21:
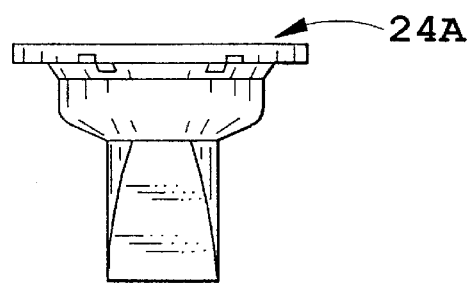
Figure 22:
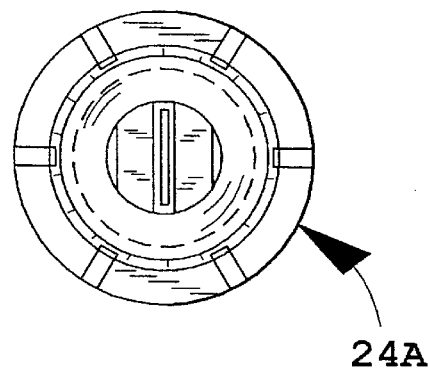
Figure 23:
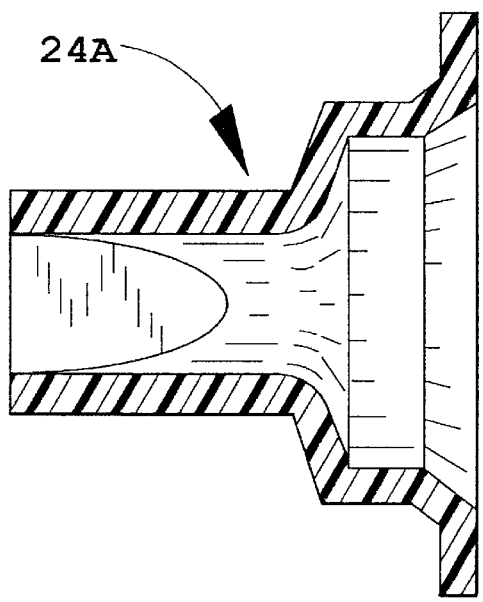
FIGS. 23–24 are cross-sectional views taken along the lines XXIII—XXIII and XXIV—XXIV in FIG. 19.
Figure 24:
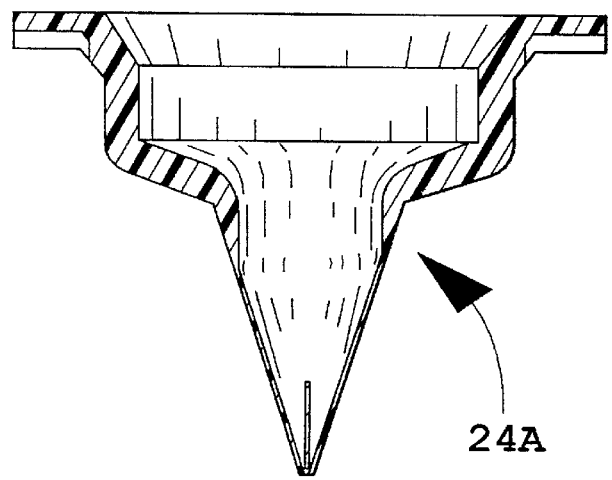
Figure 25:
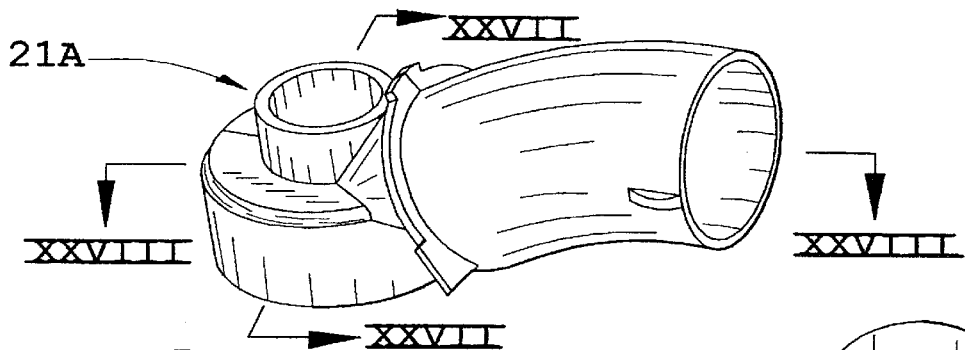
FIG. 25 is a perspective view of the pump body shown in FIG. 18.
Figure 26:
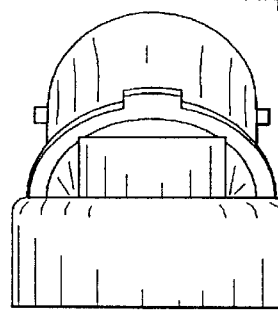
FIG. 26 is an end view of the pump body shown in FIG. 25.
Figure 27:
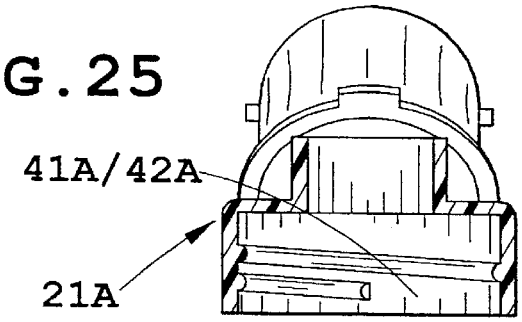
FIGS. 27–28 are cross-sectional views taken along the lines XXVII—XXVII and XXVIII—XXVIII in FIG. 25.
Figure 28:
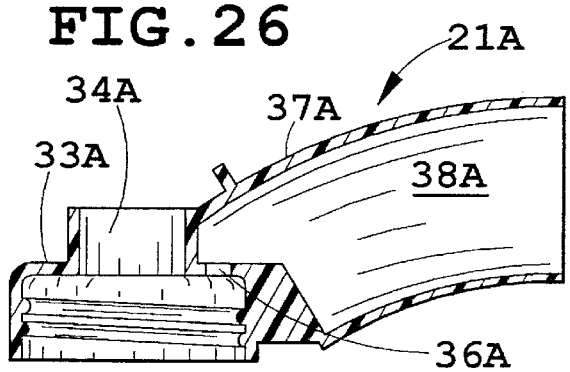
Figure 29:
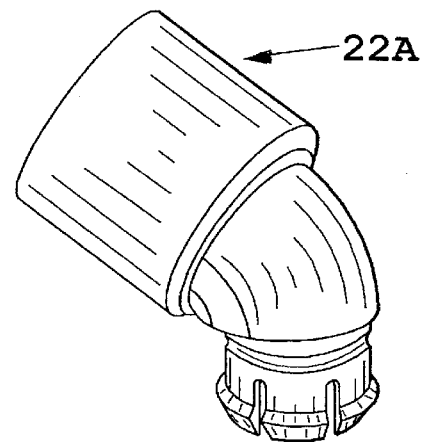
FIG. 29 is a perspective of the funnel supporting shield neck shown in FIG. 18.
Figure 30:
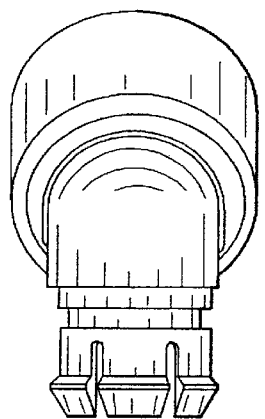
FIG. 30 is an end view of the shield neck shown in FIG. 29.
Figure 31:
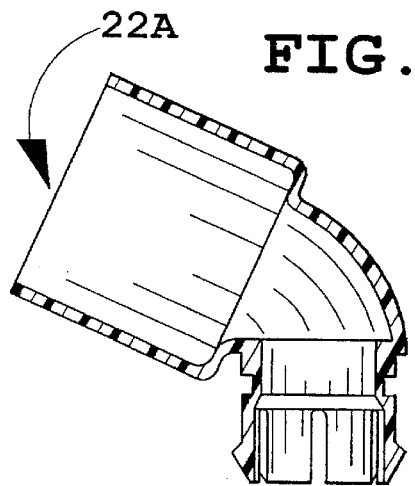
FIG. 31 is a cross-sectional view taken along the lines XXXI—XXXI in FIG. 30.
Figure 39:
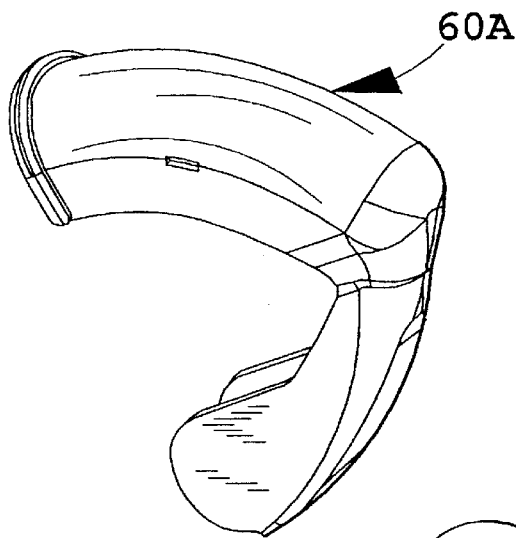
FIGS. 39–40 are perspective views of the stationary handle shown in FIG. 18.
Figure 40:
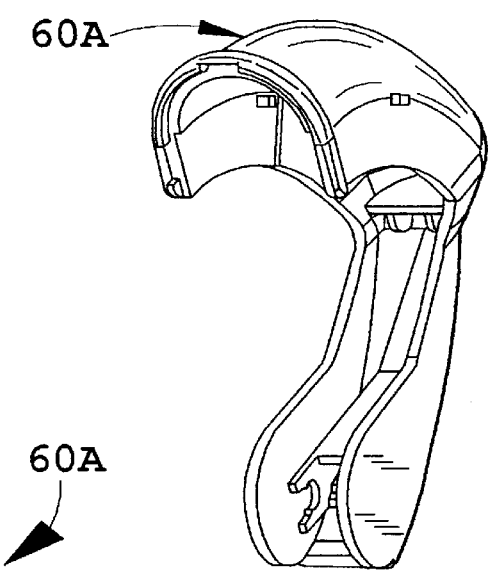
Figure 41:
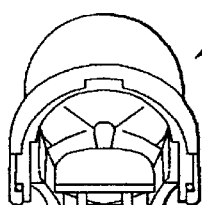
FIGS. 41–42 are front and rear views of the stationary handle shown in FIG. 39.
Figure 42:
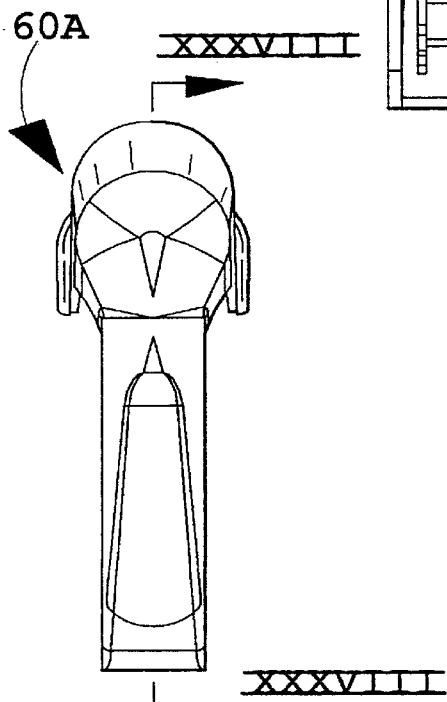
Figure 43:
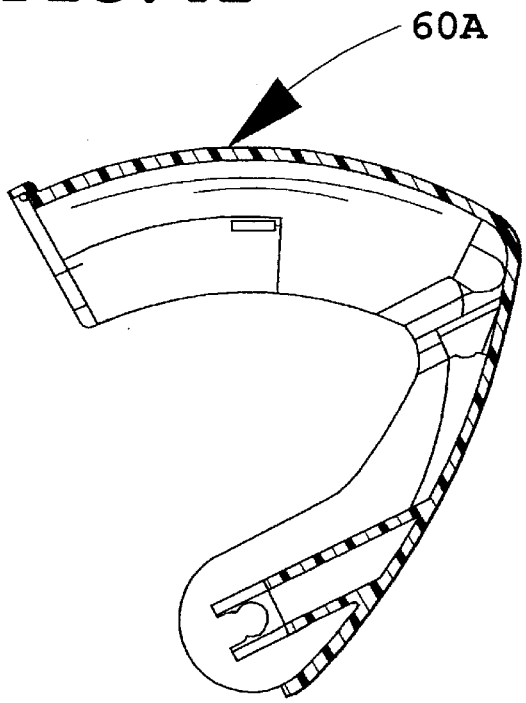
FIG. 43 is a cross-sectional view taken along the plane XLIII—XLIII in FIG. 42.

A modified manual breast pump 20A embodying the present invention is shown in FIGS. 18–43. Identical or similar parts are identified with the same identification numbers as were used for pump 20, but with the addition of a letter "A" to reduce redundant discussion. Modified manual breast pump 20A (FIG. 18) embodying the present invention includes a pump body 21A (FIGS. 25–28), a funnel supporting shield neck 22A (FIGS. 29–31), and funnel 23A (FIG. 18) connected to an inlet on the pump body 21A, and a manually operable hand-pump mechanism 25A (FIG. 18) connected to a vacuum port on the pump body 21A. The hand-pump mechanism 25A includes a spring element 61A' (FIGS. 32–34) that is releasably snap-attached to the piston element 61A" (FIGS. 35–38), which components are preassembled and then snap-attached to the stationary handle 60A (FIGS. 39–43). The breast pump 20A can be connected to a bottle 26A and conveniently and comfortably operated to extract milk from a mother's breast. The breast pump 20A is configured to stably rest on a support surface when the mother has filled the bottle 26A until the mother is ready to take care of the collected milk. The breast pump 20A is configured to be separated into components that can be sanitarily cleaned in an automatic dishwasher.

In pump 20A, pump body 21A is modified to open the cavity 41A/42A by eliminating the lower portion of walls that extend into cavity 41A/42A. Also in pump mechanism 25A, spring/piston handle 61A is modified to include the spring element 61A' that is releasably snap-attachable to piston element 61A". Specifically, spring element 61A' includes a configured end 90A having shoulders 91A for engaging pivot forming pin 84A and a projecting section of material 92A for engaging window 93A in stationary handle 61A". The releasability of spring element 61A' allows replacement of the stationary handle 61A".

Vacuum port 36A (FIG. 28) is defined by an aperture in top wall 33A adjacent to tubular sleeve 37A to provide fluid communication between inlet 34A and the pump chamber 38A.

Thus a manually operable breast pump is provided including a pump body, a funnel-supporting neck and funnel connected to an inlet on the pump body, a back splash valve connected to an outlet of the pump body, and a manually operable hand-pump mechanism connected to a vacuum port on the pump body. The breast pump can be connected to a bottle and conveniently operated to extract milk from a mother's breast. The breast pump is configured to stably rest on a support surface when the mother has filled the bottle until the mother is ready to take care of the collected milk. The breast pump is also configured to be separated into components that can be sanitarily cleaned, such as in an automatic dishwasher.

Having described the invention, it should be understood that although a preferred embodiment has been disclosed herein other modifications and embodiments can be utilized without departing from the spirit of this invention. Therefore, this invention should not be limited to only the embodiment illustrated.

The embodiments of the invention in which an exclusive property or privilege is claimed are defined as follows:

1. A manual breast pump comprising:
   a pump body defining an inlet, an outlet and a vacuum port, the outlet defining structure for sealingly engaging an opening in a milk-receiving vessel;
   a pump chamber in fluid communication with the vacuum port;
   a movable handle configured for removable snap attachment to the manual breast pump; and
   a piston disposed within the pump chamber, the piston being operably connected to the movable handle so that movement of the movable handle with respect to the pump body results in movement of the piston within the pump chamber to create a vacuum at the vacuum port.

2. The manual breast pump of claim 1, wherein the piston is an integral portion of the movable handle.

3. The manual breast pump of claim 1, further comprising a tubular neck configured at one end to sealingly frictionally engage the pump body inlet, and an inner surface at another end for receiving and frictionally engaging a slip-fit cylindrically shaped end of a breast engaging funnel, whereby the neck can be quickly attached or separated from the pump body, and the breast engaging further can be quickly attached or separated from the neck to facilitate cleaning and sanitizing of the manual breast pump.

4. The manual breast pump of claim 3, wherein the tubular neck is rotatably connected to the pump body inlet.

5. The manual breast pump of claim 3, wherein the tubular neck further includes a cylindrical recess for receiving at least one O-ring seal.

6. The manual breast pump of claim 1, further comprising a stationary handle, the movable handle being spaced from the stationary handle so that both handles can be grasped simultaneously between the palm and fingers of a hand, and wherein the movable handle is movable with respect to the stationary handle.

7. The manual breast pump of claim 6, wherein one of the handles is configured for snap attachment to the other handle, and wherein the movable handle is pivotable with respect to the stationary handle.

8. The manual breast pump of claim 7, wherein the stationary handle is configured for snap attachment to the pump body.

9. The manual breast pump of claim 8, wherein one of the stationary handle or the pump body includes at least one aperture and the other of the stationary handle and the pump body includes at least one detent adapted to be received within the aperture to facilitate snap attachment of the stationary handle to the pump body.

10. A manual breast pump, comprising:
    a pump body defining an inlet, an outlet and a vacuum port, the outlet defining structure for sealingly engaging an opening in a milk-receiving vessel;
    a pump chamber in fluid communication with the vacuum port;
    a movable handle connected to the manual breast pump;
    a piston disposed within the pump chamber, the piston being operably connected to the movable handle so that movement of the movable handle with respect to the pump body results in movement of the piston within the pump chamber to create a vacuum at the vacuum port; and
    an elastomeric back splash valve which allows milk to flow from the outlet in the pump body and into a milk-receiving vessel, but which prevents milk from flowing in the opposite direction.

11. The manual breast pump of claim 10, wherein the back splash valve includes an annular seal lip for sealing between the outlet of the pump body and upper edges of a milk-receiving vessel.

12. The manual breast pump of claim 10, wherein the back splash valve includes a pair of opposing flexible lips which flex apart to allow milk to flow through the valve from the pump body into a milk-receiving vessel, but which collapse together to prevent milk from flowing in the opposite direction.

13. The manual breast pump of claim 10, wherein the back splash valve is a single piece.

14. In a manual breast pump of the type having a piston reciprocating in a cylinder to create a vacuum at an inlet, the improvement of a two-piece actuator handle, comprising:
    a stationary handle member having an inverted generally L-shaped side elevational configuration with a normally generally horizontal leg portion thereof connected with said pump and a normally generally vertical leg portion thereof shaped for grasping; and
    a movable handle member having a lower portion thereof pivotally connected with a lower end of the vertical leg portion of said stationary handle member, a medial portion shaped for grasping, and an upper portion connected with one of said piston and said cylinder, whereby said two-piece handle is grasped and squeezed to pivot said movable handle rearwardly about said lower portion thereof toward said stationary handle thereby creating a vacuum at said inlet.

15. A manual breast pump as set forth in claim 14, including:
    a spring member biasing said movable handle member away from said stationary handle member to a normally extended position.

16. A manual breast pump as set forth in claim 15, wherein:
    said spring member is juxtaposed between said movable handle member and said stationary handle member.

17. A manual breast pump as set forth in claim 16, wherein:
    said spring member comprises a leaf spring.

18. A manual breast pump as set forth in claim 17, wherein:
    said leaf spring is formed integrally with said movable handle member, and includes a free end thereof which engages said stationary handle member.

19. A manual breast pump as set forth in claim 18, wherein:
said stationary handle member includes a contoured exterior surface along said vertical leg portion shaped for engaging the palm of the user.

20. A manual breast pump as set forth in claim 19, wherein:
said movable handle member includes a contoured exterior surface, facing opposite said contoured exterior surface of said stationary handle member, shaped for engaging the fingers of the user.

21. A manual breast pump as set forth in claim 20, wherein:
said contoured exterior surface of said movable handle member includes a finger notch disposed adjacent an upper portion thereof.

22. A manual breast pump as set forth in claim 21, wherein:
said movable handle member is pivotally connected with said stationary handle member by a snap attachment.

23. A manual breast pump as set forth in claim 22, wherein:
said stationary handle member is connected with said pump by a snap attachment.

24. A manual breast pump as set forth in claim 23, wherein:
said piston is formed integrally with said movable handle member.

25. A manual breast pump as set forth in claim 24, wherein:
said cylinder has an arcuate side elevational shape.

26. A manual breast pump as set forth in claim 14, wherein:
said stationary handle member includes a contoured exterior surface along said vertical leg portion shaped for engaging the palm of the user.

27. A manual breast pump as set forth in claim 14, wherein:
said movable handle member includes a contoured exterior surface, facing opposite said contoured exterior surface of said stationary handle member, shaped for engaging the fingers of the user.

28. A manual breast pump as set forth in claim 14, wherein:
said movable handle member is pivotally connected with said stationary handle member by a snap attachment.

29. A manual breast pump as set forth in claim 14, wherein:
said stationary handle member is connected with said pump by a snap attachment.

30. A manual breast pump as set forth in claim 14, wherein:
said piston is formed integrally with said movable handle member.

31. A manual breast pump as set forth in claim 14, wherein:
said cylinder has an arcuate side elevational shape.

32. A manual breast pump as set forth in claim 1, wherein:
said pump body includes an inner annular recess, and an outer annular recess.

33. A manual breast pump as set forth in claim 32, wherein:
said movable handle includes a stationary handle member, a movable handle member, and an integrally formed leaf spring biasing said movable handle member away from said stationary handle member to a normally extended position.

* * * * *